(12) United States Patent
Marinkovic et al.

(10) Patent No.: US 12,156,673 B2
(45) Date of Patent: Dec. 3, 2024

(54) TEMPERATURE MEASUREMENT DEVICE FOR A HANDPIECE OF A SURGICAL INSTRUMENT

(71) Applicant: Covidien LP, Mansfield, MA (US)

(72) Inventors: Aleksandar Marinkovic, Brookline, MA (US); Dale E. Whipple, Nashua, NH (US); Jordan A. Whisler, Brookline, MA (US)

(73) Assignee: Covidien LP, Mansfield, MA (US)

(*) Notice: Subject to any disclaimer, the term of this patent is extended or adjusted under 35 U.S.C. 154(b) by 392 days.

(21) Appl. No.: 17/471,665

(22) Filed: Sep. 10, 2021

(65) Prior Publication Data

US 2022/0104844 A1 Apr. 7, 2022

Related U.S. Application Data

(60) Provisional application No. 63/088,562, filed on Oct. 7, 2020.

(51) Int. Cl.
*A61B 17/32* (2006.01)
*A61B 1/015* (2006.01)
(Continued)

(52) U.S. Cl.
CPC ........ *A61B 17/32002* (2013.01); *A61B 1/015* (2013.01); *A61B 17/42* (2013.01);
(Continued)

(58) Field of Classification Search
CPC ... A61B 17/32002; A61B 1/015; A61B 17/42; A61B 2562/0271; G01J 5/10
See application file for complete search history.

(56) References Cited

U.S. PATENT DOCUMENTS 1,585,934 A 5/1926 Muir
1,666,332 A 4/1928 Hirsch
(Continued)

FOREIGN PATENT DOCUMENTS

DE 3339322 A1 5/1984
DE 3206381 C2 7/1986
(Continued)

OTHER PUBLICATIONS

Extended European Search Report issued in corresponding application EP 21200097.0 dated Mar. 1, 2022 (8 pages).

*Primary Examiner* — Thomas McEvoy
(74) *Attorney, Agent, or Firm* — Carter, DeLuca & Farrell LLP

(57) ABSTRACT

A surgical instrument includes a handpiece including a housing and a motor disposed in the housing. An end effector assembly is operably coupled to the handpiece. The motor actuates the end effector assembly. A temperature measurement assembly is in the housing. The temperature measurement assembly measures a temperature of the motor. The temperature measurement assembly includes a printed circuit board (PCB) including an orifice extending through the PCB. An infrared (IR) sensor is on the PCB. The IR sensor transmits IR light to a temperature measurement location of the motor through the orifice of the PCB. The IR sensor detects IR light reflected from the temperature measurement location of the motor to determine a temperature of the temperature measurement location of the motor.

13 Claims, 3 Drawing Sheets

(51) Int. Cl.
*A61B 17/42* (2006.01)
*G01J 5/10* (2006.01)

(52) U.S. Cl.
CPC .......... *G01J 5/10* (2013.01); *A61B 2017/4216* (2013.01); *A61B 2217/005* (2013.01); *A61B 2562/0271* (2013.01); *A61B 2562/227* (2013.01)

(56) References Cited

U.S. PATENT DOCUMENTS

| | | | |
|---|---|---|---|
| 1,831,786 A | 11/1931 | Duncan | |
| 2,708,437 A | 5/1955 | Hutchins | |
| 3,297,022 A | 1/1967 | Wallace | |
| 3,686,706 A | 8/1972 | Finley | |
| 3,734,099 A | 5/1973 | Bender et al. | |
| 3,791,379 A | 2/1974 | Storz | |
| 3,812,855 A | 5/1974 | Banko | |
| 3,835,842 A | 9/1974 | Iglesias | |
| 3,850,162 A | 11/1974 | Iglesias | |
| 3,945,375 A | 3/1976 | Banko | |
| 3,980,252 A | 9/1976 | Tae | |
| 3,995,619 A | 12/1976 | Glatzer | |
| 3,996,921 A | 12/1976 | Neuwirth | |
| 4,011,869 A | 3/1977 | Seiler, Jr. | |
| 4,108,182 A | 8/1978 | Hartman et al. | |
| 4,146,405 A | 3/1979 | Timmer et al. | |
| 4,198,958 A | 4/1980 | Utsugi | |
| 4,203,444 A | 5/1980 | Bonnell et al. | |
| 4,210,146 A | 7/1980 | Banko | |
| 4,246,902 A | 1/1981 | Martinez | |
| 4,247,180 A | 1/1981 | Norris | |
| 4,258,721 A | 3/1981 | Parent et al. | |
| 4,261,346 A | 4/1981 | Wettermann | |
| 4,294,234 A | 10/1981 | Matsuo | |
| 4,316,465 A | 2/1982 | Dotson, Jr. | |
| 4,369,768 A | 1/1983 | Vukovic | |
| 4,392,485 A | 7/1983 | Hiltebrandt | |
| 4,414,962 A | 11/1983 | Carson | |
| 4,449,538 A | 5/1984 | Corbitt et al. | |
| 4,493,698 A | 1/1985 | Wang et al. | |
| 4,517,977 A | 5/1985 | Frost | |
| 4,543,965 A | 10/1985 | Pack et al. | |
| 4,567,880 A | 2/1986 | Goodman | |
| 4,589,414 A | 5/1986 | Yoshida et al. | |
| 4,601,284 A | 7/1986 | Arakawa et al. | |
| 4,601,290 A | 7/1986 | Effron et al. | |
| 4,606,330 A | 8/1986 | Bonnet | |
| 4,630,598 A | 12/1986 | Bonnet | |
| 4,644,952 A | 2/1987 | Patipa et al. | |
| 4,649,919 A | 3/1987 | Thimsen et al. | |
| 4,700,694 A | 10/1987 | Shishido | |
| 4,706,656 A | 11/1987 | Kuboto | |
| 4,718,291 A | 1/1988 | Wood et al. | |
| 4,737,142 A | 4/1988 | Heckele | |
| 4,749,376 A | 6/1988 | Kensey et al. | |
| 4,756,309 A | 7/1988 | Sachse et al. | |
| 4,819,635 A | 4/1989 | Shapiro | |
| 4,844,064 A | 7/1989 | Thimsen et al. | |
| 4,850,354 A | 7/1989 | McGurk-Burleson et al. | |
| 4,856,919 A | 8/1989 | Takeuchi et al. | |
| 4,867,157 A | 9/1989 | McGurk-Burleson et al. | |
| 4,924,851 A | 5/1990 | Ognier et al. | |
| 4,940,061 A | 7/1990 | Terwilliger et al. | |
| 4,950,278 A | 8/1990 | Sachse et al. | |
| 4,955,882 A | 9/1990 | Hakky | |
| 4,971,034 A | 11/1990 | Doi et al. | |
| 4,986,827 A | 1/1991 | Akkas et al. | |
| 4,998,527 A | 3/1991 | Meyer | |
| 4,998,914 A | 3/1991 | Wiest et al. | |
| 5,007,917 A | 4/1991 | Evans | |
| 5,027,792 A | 7/1991 | Meyer | |
| 5,037,386 A | 8/1991 | Marcus et al. | |
| 5,105,800 A | 4/1992 | Takahashi et al. | |
| 5,106,364 A | 4/1992 | Hayafuji et al. | |
| 5,112,299 A | 5/1992 | Pascaloff | |
| 5,116,868 A | 5/1992 | Chen et al. | |
| 5,125,910 A | 6/1992 | Freitas | |
| 5,133,713 A | 7/1992 | Huang et al. | |
| 5,152,744 A | 10/1992 | Krause et al. | |
| 5,158,553 A | 10/1992 | Berry et al. | |
| 5,163,433 A | 11/1992 | Kagawa et al. | |
| 5,169,397 A | 12/1992 | Sakashita et al. | |
| 5,176,677 A | 1/1993 | Wuchinich | |
| 5,195,541 A | 3/1993 | Obenchain | |
| 5,226,910 A | 7/1993 | Kajiyama et al. | |
| 5,244,459 A | 9/1993 | Hill | |
| 5,254,117 A | 10/1993 | Rigby et al. | |
| 5,269,785 A | 12/1993 | Bonutti | |
| 5,270,622 A | 12/1993 | Krause | |
| 5,275,609 A | 1/1994 | Pingleton et al. | |
| 5,288,290 A | 2/1994 | Brody | |
| 5,304,118 A | 4/1994 | Trese et al. | |
| 5,312,399 A | 5/1994 | Hakky et al. | |
| 5,312,425 A | 5/1994 | Evans et al. | |
| 5,312,430 A | 5/1994 | Rosenbluth et al. | |
| 5,320,091 A | 6/1994 | Grossi et al. | |
| 5,347,992 A | 9/1994 | Pearlman et al. | |
| 5,350,390 A | 9/1994 | Sher | |
| 5,364,395 A | 11/1994 | West, Jr. | |
| 5,374,253 A | 12/1994 | Burns, Sr. et al. | |
| 5,390,585 A | 2/1995 | Ryuh | |
| 5,392,765 A | 2/1995 | Muller | |
| 5,395,313 A | 3/1995 | Naves et al. | |
| 5,403,276 A | 4/1995 | Schechter et al. | |
| 5,409,013 A | 4/1995 | Clement | |
| 5,409,453 A | 4/1995 | Lundquist et al. | |
| 5,411,513 A | 5/1995 | Ireland et al. | |
| 5,421,819 A | 6/1995 | Edwards et al. | |
| 5,425,376 A | 6/1995 | Banys et al. | |
| 5,429,601 A | 7/1995 | Conley et al. | |
| 5,435,805 A | 7/1995 | Edwards et al. | |
| 5,443,476 A | 8/1995 | Shapiro | |
| 5,449,356 A | 9/1995 | Walbrink et al. | |
| 5,456,673 A | 10/1995 | Ziegler et al. | |
| 5,456,689 A | 10/1995 | Kresch et al. | |
| 5,483,951 A | 1/1996 | Frassica et al. | |
| 5,490,819 A | 2/1996 | Nicholas et al. | |
| 5,490,860 A | 2/1996 | Middle et al. | |
| 5,492,537 A | 2/1996 | Vancaillie | |
| 5,498,258 A | 3/1996 | Hakky et al. | |
| 5,527,331 A | 6/1996 | Kresch et al. | |
| 5,549,541 A | 8/1996 | Muller | |
| 5,556,378 A | 9/1996 | Storz et al. | |
| 5,563,481 A | 10/1996 | Krause | |
| 5,569,164 A | 10/1996 | Lurz | |
| 5,569,254 A | 10/1996 | Carlson et al. | |
| 5,569,284 A | 10/1996 | Young et al. | |
| 5,575,756 A | 11/1996 | Karasawa et al. | |
| 5,586,973 A | 12/1996 | Lemaire et al. | |
| 5,591,187 A | 1/1997 | Dekel | |
| 5,601,583 A | 2/1997 | Donahue et al. | |
| 5,601,603 A | 2/1997 | Illi | |
| 5,602,449 A | 2/1997 | Krause et al. | |
| 5,603,332 A | 2/1997 | O'Connor | |
| 5,624,590 A * | 4/1997 | Fiory | G01J 5/0003 118/724 |
| 5,630,798 A | 5/1997 | Beiser et al. | |
| 5,649,547 A | 7/1997 | Ritchart et al. | |
| 5,669,927 A | 9/1997 | Boebel et al. | |
| 5,672,945 A | 9/1997 | Krause | |
| 5,674,179 A | 10/1997 | Bonnet et al. | |
| 5,676,497 A | 10/1997 | Kim | |
| 5,695,448 A | 12/1997 | Kimura et al. | |
| 5,702,420 A | 12/1997 | Sterling et al. | |
| 5,709,698 A | 1/1998 | Adams et al. | |
| 5,730,752 A | 3/1998 | Alden et al. | |
| 5,733,298 A | 3/1998 | Berman et al. | |
| 5,741,286 A | 4/1998 | Recuset | |
| 5,741,287 A | 4/1998 | Alden et al. | |
| 5,749,885 A | 5/1998 | Sjostrom et al. | |
| 5,749,889 A | 5/1998 | Bacich et al. | |
| 5,759,185 A | 6/1998 | Grinberg | |
| 5,772,634 A | 6/1998 | Atkinson | |

(56) References Cited

U.S. PATENT DOCUMENTS

| | | |
|---|---|---|
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,025,656 B2 | 9/2011 | Gruber et al. |
| 8,061,359 B2 | 11/2011 | Emanuel |
| 8,062,214 B2 | 11/2011 | Shener et al. |
| 8,419,626 B2 | 4/2013 | Shener-Irmakoglu et al. |
| 8,465,421 B2 | 6/2013 | Finkman et al. |
| 8,528,563 B2 | 9/2013 | Gruber |
| 8,574,253 B2 | 11/2013 | Gruber et al. |
| 8,647,349 B2 | 2/2014 | Gruber et al. |
| 8,663,264 B2 | 3/2014 | Cesarini et al. |
| 8,678,999 B2 | 3/2014 | Isaacson |
| 8,790,303 B2 | 7/2014 | Williams et al. |
| 8,834,487 B2 | 9/2014 | Gruber et al. |
| 8,840,625 B2 | 9/2014 | Adams et al. |
| 8,840,626 B2 | 9/2014 | Adams et al. |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,060,760 B2 | 6/2015 | Sullivan et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,095,366 B2 | 8/2015 | Sullivan et al. |
| 9,125,550 B2 | 9/2015 | Shener-Irmakoglu et al. |
| 9,155,454 B2 | 10/2015 | Sahney et al. |
| 9,259,233 B2 | 2/2016 | Gruber et al. |
| 9,653,935 B2 * | 5/2017 | Cong ............... H02J 7/007192 |
| 10,085,751 B2 | 10/2018 | Overmyer et al. |
| 10,420,554 B2 | 9/2019 | Collings et al. |
| 2007/0085496 A1 * | 4/2007 | Philipp ............... A61B 17/151 |
| | | 318/139 |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber et al. |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0082628 A1 | 3/2009 | Kucklick et al. |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0087798 A1 | 4/2010 | Adams et al. |
| 2010/0152647 A1 | 6/2010 | Shener et al. |
| 2011/0034943 A1 | 2/2011 | Churchill et al. |
| 2011/0077674 A1 | 3/2011 | Sullivan et al. |
| 2011/0118544 A1 | 5/2011 | Adams et al. |
| 2011/0166419 A1 | 7/2011 | Reif et al. |
| 2012/0067352 A1 | 3/2012 | Gruber et al. |
| 2012/0078038 A1 | 3/2012 | Sahney et al. |
| 2013/0131452 A1 | 5/2013 | Kuroda et al. |
| 2014/0003183 A1 | 1/2014 | Song |
| 2014/0072930 A1 * | 3/2014 | Pruckner ............... G01K 13/00 |
| | | 433/27 |
| 2015/0013315 A1 * | 1/2015 | Frederiksen ............ G01J 5/0022 |
| | | 60/299 |
| 2016/0041038 A1 * | 2/2016 | Geiger ............... G01J 5/0806 |
| | | 250/338.1 |
| 2016/0066945 A1 | 3/2016 | Nguyen et al. |
| 2019/0254506 A1 | 8/2019 | Hamm et al. |
| 2020/0268362 A1 * | 8/2020 | Van Liere ............ A61B 10/0266 |

FOREIGN PATENT DOCUMENTS

| | | |
|---|---|---|
| DE | 3601453 A1 | 9/1986 |
| DE | 3615694 A1 | 11/1987 |
| DE | 4038398 A1 | 6/1992 |
| DE | 4440035 A1 | 5/1996 |
| DE | 19633124 A1 | 5/1997 |
| DE | 19751632 C1 | 9/1999 |

(56) References Cited

FOREIGN PATENT DOCUMENTS

| | | |
|---|---:|---|
| DE | 102006022827 A1 | 12/2006 |
| EP | 0310285 A2 | 4/1989 |
| EP | 0327410 A1 | 8/1989 |
| EP | 0557044 A1 | 8/1993 |
| EP | 0582295 A2 | 2/1994 |
| EP | 0606531 A2 | 7/1994 |
| EP | 0621008 A2 | 10/1994 |
| EP | 0806183 A1 | 11/1997 |
| EP | 1681022 A1 | 7/2006 |
| EP | 2524667 A2 | 11/2012 |
| EP | 2939607 A1 | 11/2015 |
| EP | 3711691 A1 | 9/2020 |
| GB | 2093353 A | 9/1982 |
| GB | 2311468 A | 10/1997 |
| JP | 2001075416 A | 3/2001 |
| JP | 2002529185 A | 9/2002 |
| JP | 2002538889 A | 11/2002 |
| JP | 2003245247 A | 9/2003 |
| NL | 1006944 C2 | 3/1999 |
| WO | 8101648 A1 | 6/1981 |
| WO | 9211816 A2 | 7/1992 |
| WO | 9307821 A1 | 4/1993 |
| WO | 9315664 A1 | 8/1993 |
| WO | 9426181 A1 | 11/1994 |
| WO | 9505777 A1 | 3/1995 |
| WO | 9510981 A1 | 4/1995 |
| WO | 9510982 A1 | 4/1995 |
| WO | 9522935 A1 | 8/1995 |
| WO | 9530377 A1 | 11/1995 |
| WO | 9611638 A1 | 4/1996 |
| WO | 9626676 A1 | 9/1996 |
| WO | 9709922 A1 | 3/1997 |
| WO | 9717027 A1 | 5/1997 |
| WO | 9719642 A1 | 6/1997 |
| WO | 9724071 A1 | 7/1997 |
| WO | 9734534 A1 | 9/1997 |
| WO | 9735522 A1 | 10/1997 |
| WO | 9809569 A1 | 3/1998 |
| WO | 9810707 A1 | 3/1998 |
| WO | 9846147 A1 | 10/1998 |
| WO | 9903407 A1 | 1/1999 |
| WO | 9903409 A1 | 1/1999 |
| WO | 9907295 A1 | 2/1999 |
| WO | 9911184 A1 | 3/1999 |
| WO | 9939648 A1 | 8/1999 |
| WO | 9944506 A1 | 9/1999 |
| WO | 9960935 A1 | 12/1999 |
| WO | 0012010 A1 | 3/2000 |
| WO | 0028890 A1 | 5/2000 |
| WO | 0033743 A1 | 6/2000 |
| WO | 0044295 A1 | 8/2000 |
| WO | 0047116 A1 | 8/2000 |
| WO | 0057797 A1 | 10/2000 |
| WO | 0135831 A1 | 5/2001 |
| WO | 0158368 A1 | 8/2001 |
| WO | 0160261 A2 | 8/2001 |
| WO | 0195810 A2 | 12/2001 |
| WO | 02069808 A2 | 9/2002 |
| WO | 03022164 A1 | 3/2003 |
| WO | 03077767 A1 | 9/2003 |
| WO | 2005060842 A1 | 7/2005 |
| WO | 2005096963 A2 | 10/2005 |
| WO | 2006105283 A2 | 10/2006 |
| WO | 2006121968 A2 | 11/2006 |
| WO | 2006121970 A2 | 11/2006 |
| WO | 2007044833 A2 | 4/2007 |
| WO | 2012044705 A1 | 4/2012 |

\* cited by examiner

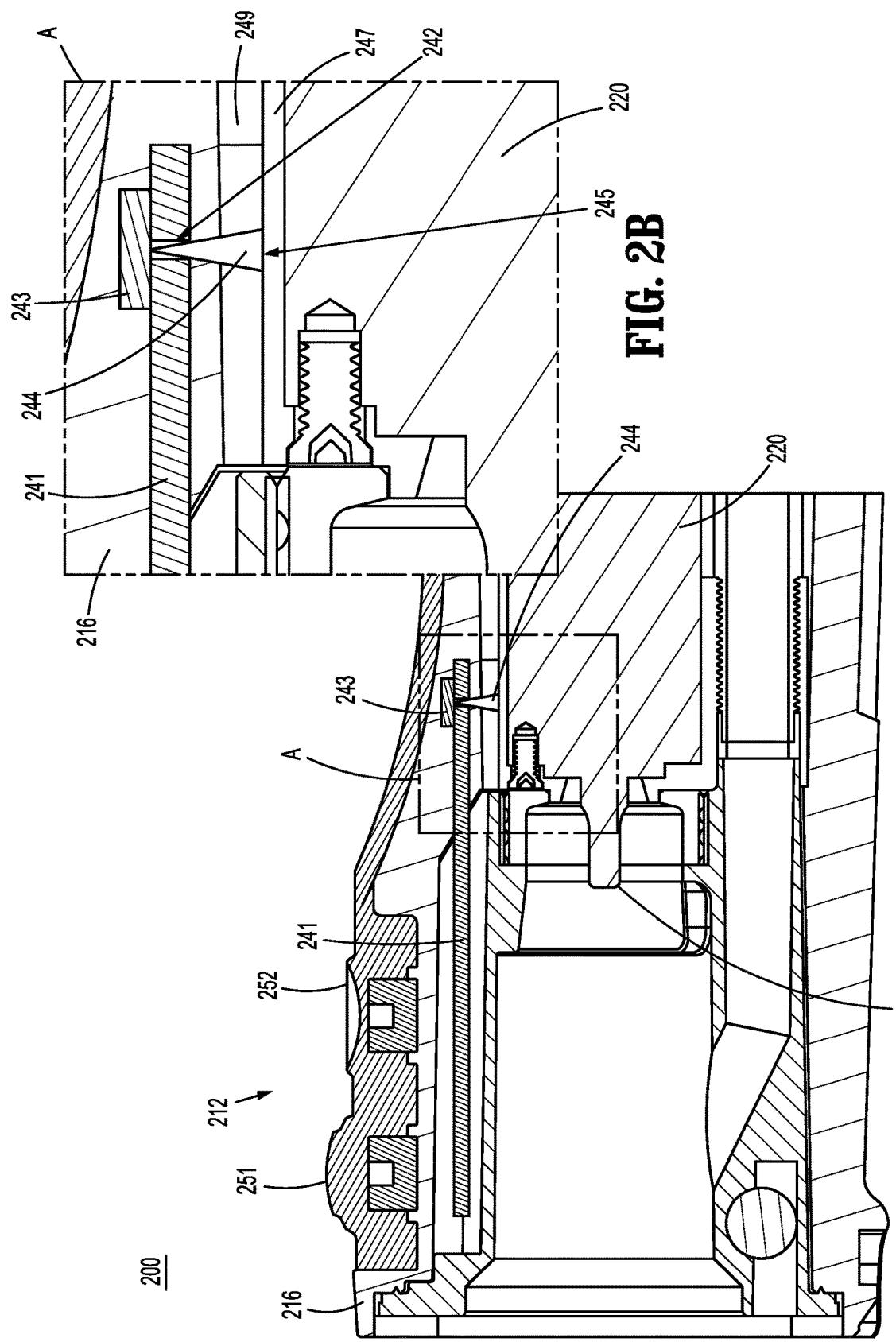

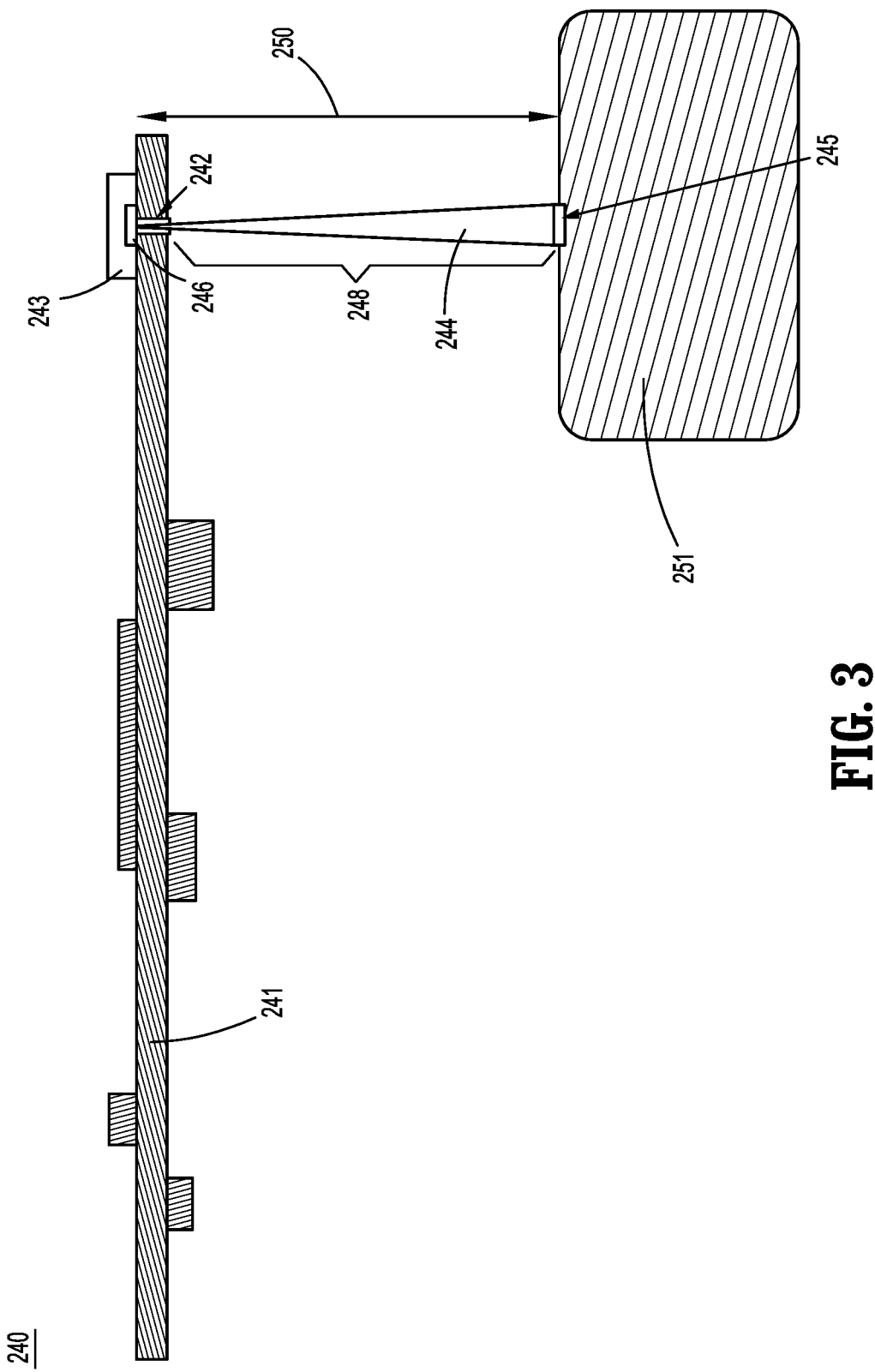

TEMPERATURE MEASUREMENT DEVICE FOR A HANDPIECE OF A SURGICAL INSTRUMENT

CROSS-REFERENCE TO RELATED APPLICATIONS

This application claims the benefit of and priority to U.S. Provisional Patent Application 63/088,562, filed Oct. 7, 2020, the entire contents of which is incorporated by reference herein.

FIELD

The present disclosure relates to a temperature measurement device and, more specifically, to a temperature measurement device for a handpiece of a surgical instrument.

BACKGROUND

Surgical procedures, such as hysteroscopic surgical procedures, may be performed endoscopically within an organ, such as a uterus, by inserting an endoscope into the uterus and passing a tissue resection device through the endoscope and into the uterus. With respect to such hysteroscopic tissue resection procedures, it often is desirable to distend the uterus with a fluid, for example, saline, sorbitol, or glycine. The inflow and outflow of the fluid during the procedure maintains the uterus in a distended state and flushes tissue and other debris from within the uterus to maintain a visible working space. The outflow fluid is collected by a collection system.

SUMMARY

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

Provided in accordance with aspects of the present disclosure is a surgical instrument including a handpiece. The handpiece includes a housing and a motor disposed in the housing. An end effector assembly is operably coupled to the handpiece. The motor actuates the end effector assembly. A temperature measurement assembly is in the housing. The temperature measurement assembly measures a temperature of the motor. The temperature measurement assembly includes a printed circuit board (PCB) including an orifice extending through the PCB. An infrared (IR) sensor is on the PCB. The IR sensor transmits IR light to a temperature measurement location of the motor through the orifice of the PCB. The IR sensor detects IR light reflected from the temperature measurement location of the motor to determine a temperature of the temperature measurement location of the motor.

In an aspect of the present disclosure, the IR sensor includes an IR filter. The IR sensor transmits the IR light through the IR filter. The IR filter is on the PCB and extends across the orifice of the PCB.

In an aspect of the present disclosure, the temperature measurement location of the motor is on an outer housing of the motor.

In an aspect of the present disclosure, the IR sensor is positioned to transmit IR light across an air gap between the PCB and the temperature measurement location of the motor.

In an aspect of the present disclosure, a substantially transparent spacer is positioned between the PCB and the motor. The IR sensor transmits the IR light across the transparent spacer to the temperature measurement location of the motor.

In an aspect of the present disclosure, the substantially transparent spacer is formed of silicone.

In an aspect of the present disclosure, an output coupler is operably coupled to the motor, and the IR sensor transmits IR light to a temperature measurement location of the output coupler to determine a temperature of the temperature measurement location of the output coupler.

BRIEF DESCRIPTION OF THE DRAWINGS

Various aspects and features of the present disclosure are described hereinbelow with reference to the drawings wherein:

FIG. 2A is a cross-sectional view of a temperature measurement assembly in a handpiece of a surgical instrument in accordance with the present disclosure;

FIG. 2B is an enlarged cross-sectional view of area "A" of FIG. 2A; and

FIG. 3 is a layout view of the temperature measurement assembly of FIG. 2A.

DETAILED DESCRIPTION

Figure 1:
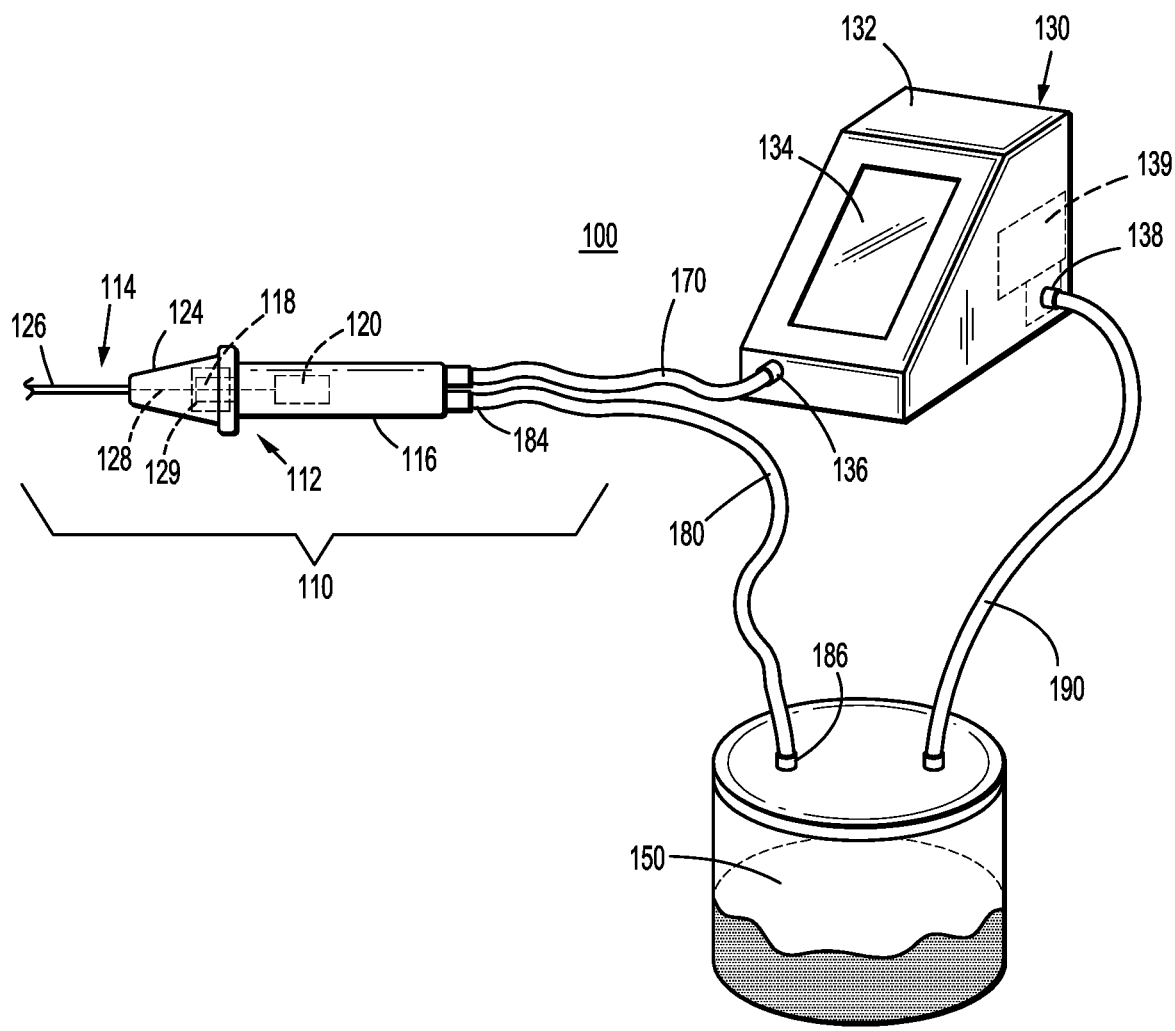
FIG. 1 is a perspective view of a surgical instrument in accordance with the present disclosure.

Descriptions of technical features or aspects of an exemplary configuration of the disclosure should typically be considered as available and applicable to other similar features or aspects in another exemplary configuration of the disclosure. Accordingly, technical features described herein according to one exemplary configuration of the disclosure may be applicable to other exemplary configurations of the disclosure, and thus duplicative descriptions may be omitted herein.

Exemplary configurations of the disclosure will be described more fully below (e.g., with reference to the accompanying drawings). Like reference numerals may refer to like elements throughout the specification and drawings.

Referring to FIG. 1, a surgical system provided in accordance with aspects of the present disclosure is shown generally identified by reference numeral 100. Surgical system 100 includes a surgical instrument 110, a control console 130, and a collection vessel 150. Surgical system 100 further includes a cable 170, outflow tubing 180, and vacuum tubing 190. Surgical system 100 may further include an endoscope (not shown), e.g., a hysteroscope, defining a working channel for inserting of surgical instrument 110 therethrough, and adapted to connect to inflow tubing (not shown) to supply fluid to an internal surgical site and/or additional outflow tubing (not shown) to return fluid to collection vessel 150.

Surgical instrument 110 includes a handpiece 112 that may be configured as a reusable component and an end effector assembly 114 that may be configured as a single-use, disposable component. Handpiece 112 includes a housing 116 to facilitate grasping and manipulation of surgical instrument 110 by a user. Handpiece 112 further includes an output coupler 118 configured to operably engage end effector assembly 114, a motor 120 disposed within housing 116 and operably coupled to output coupler 118 to drive output coupler 118 and, thus, drive end effector assembly 114. Cable 170 electrically couples handpiece 112 and control console 130 with one another and, more specifically, electrically couples control console 130 with motor 120 to power and control operation of motor 120 and electrically couples control console 130 with a storage device(s), e.g., a microchip(s) (not explicitly shown), associated with handpiece 112 and/or end effector assembly 114 to enable communication of, for example, identification, setting, and control information therebetween. In embodiments, cable 170 is fixedly attached to handpiece 112 and releasably couplable with control console 130, although other configurations are also contemplated.

Continuing with reference to FIG. 1, end effector assembly 114 includes a proximal hub 124 configured to releasably engage housing 116 of handpiece 112 to releasably mechanically engage end effector assembly 114 with handpiece 112. End effector assembly 114 further includes an outer shaft 126 extending distally from proximal hub 124 and a cutting shaft 128 extending through outer shaft 126. A proximal end of cutting shaft 128 extends into proximal hub 124 wherein an input coupler 129 is engaged with cutting shaft 128. Input coupler 129 is configured to operably couple to output coupler 118 of handpiece 112 when proximal hub 124 is engaged with housing 116 such that, when motor 120 is activated to drive output coupler 118, input coupler 129 is driven in a corresponding manner to thereby move cutting shaft 128 within and relative to outer shaft 126.

Outer shaft 126, as noted above, extends distally from proximal hub 124 and, in embodiments, is stationary relative to proximal hub 124, although other configurations are also contemplated. Outer shaft 126 may define a window (not shown) through a side wall thereof towards a distal end thereof to provide access to cutting shaft 128 which is rotatably and/or translatably disposed within outer shaft 126. Cutting shaft 128 may define an opening (not shown) towards the distal end thereof providing access to the interior thereof and may include a serrated cutting edge (not shown) surrounding the opening, although other suitable cutting-edge configurations are also contemplated. Alternatively, or additionally, outer shaft 126 may include a cutting edge defined about the window thereof.

Motor 120, as noted above, is activated to move cutting shaft 128 and, more specifically, to drive rotation and/or translation of cutting shaft 128 relative to outer shaft 126. Control console 130, coupled to motor 120 via cable 170, enables selective powering and controlling of motor 120 and, thus, selective rotation and/or translation of cutting shaft 128 relative to outer shaft 126 to resect tissue adjacent the distal end of end effector assembly 114. Control console 130 is detailed below.

Outflow tubing 180 includes a distal end 184 configured to releasably couple to handpiece 112 and a proximal end 186 configured to couple to collection vessel 150. More specifically, handpiece 112 defines an internal passage (not shown) that couples distal end 184 of outflow tubing 180 with the interior of cutting shaft 128 in fluid communication with the interior of cutting shaft 128 such that fluid, tissue, and debris drawn into cutting shaft 128 and/or outer shaft 126 may be suctioned, under vacuum, e.g., from vacuum pump 139 of control console 130, through end effector assembly 114, handpiece 112, and outflow tubing 180 to collection vessel 150.

Referring still to FIG. 1, collection vessel 150, as noted above, is coupled to proximal end 186 of outflow tubing 180 to receive the fluid, tissue, and debris suctioned through end effector assembly 114 and outflow tubing 180. Vacuum tubing 190 is coupled between collection vessel 150 and a vacuum source, e.g., vacuum pump 139 of control console 130, such that, upon activation of vacuum pump 139, negative pressure is established through collection vessel 150, outflow tubing 180, and the interior of cutting shaft 128 of end effector assembly 114 to draw the fluids, tissue, and debris into and through cutting shaft 128, handpiece 112, outflow tubing 180, and into collection vessel 150.

Control console 130 generally includes an outer housing 132, a touch-screen display 134 accessible from the exterior of outer housing 132, a cable port 136 configured to receive cable 170, a vacuum tubing port 138 configured to receive vacuum tubing 190, and a vacuum pump 139 disposed within outer housing 132 and operably coupled with vacuum port 138. Outer housing 132 further houses internal electronics (not shown) of control console 130. Control console 130 may be configured to connect to a mains power supply (not shown) for powering control console 130. Further, control console 130 may be configured to receive user input, e.g., use information, setting selections, etc., via touch-screen display 134 or a peripheral input device (not shown) coupled to control console 130. Operational input, e.g., ON/OFF signals, power level settings (HI power vs. LO power), etc., may likewise be input via touch-screen display 134 or a peripheral input device (not shown) such as, for example, a footswitch (not shown), a handswitch (see, e.g., handswitches 251, 252 in FIG. 2A) disposed on handpiece 112, etc.

In use, upon an activation input provided to control console 130, control console 130 powers and controls motor 120 of handpiece 112 to, in turn, drive cutting shaft 128 of end effector assembly 114 to resect tissue adjacent the distal end of end effector assembly 114, while vacuum pump 139 of control console 130 suctions fluid, the resected tissue, and debris through cutting shaft 128, handpiece 112, outflow tubing 180, and into collection vessel 150.

Referring to FIGS. 2A, 2B, and 3, a surgical instrument provided in accordance with aspects of the present disclosure is shown generally identified by reference numeral 200. Surgical instrument 200 includes a handpiece 212 including a housing 216 and a motor 220 disposed in the housing 216. Unless otherwise indicate herein, the motor 220 is substantially the same as the motor 120, the handpiece 212 is substantially the same as the handpiece 112, and the housing 216 is substantially the same as the housing 116. An end effector assembly (see, e.g., end effector assembly 114 of FIG. 1) is operably coupled to the handpiece 212. The motor 220 actuates the end effector assembly.

The temperature measurement assembly 240 described below with reference to FIGS. 2A, 2B, and 3 may be positioned in the handpiece 112 of FIG. 1. For example, the infrared (IR) sensor 243 may be employed to measure a temperature of the motor 120 and/or the output coupler 118 in housing 116 of handle 112.

A temperature measurement assembly 240 is in the housing 216. The temperature measurement assembly 240 may include a digital thermophile temperature sensor or spot pyrometer. The temperature measurement assembly 240 measures a surface temperature of a component (see, e.g., component 251 in FIG. 3) within the housing 216 through an air gap 248 or a transparent spacer 249. Thus, the temperature measurement assembly 240 may be employed to measure surface temperatures within housing 216 of handpiece 212 without the use of a wired temperature sensor, provided that a clear path for an IR beam is available to the desired surface. The temperature measurement assembly 240 can measure a temperature of the motor 220. For example, a surface temperature of an outer housing 247 of the motor 220 can be measured.

The temperature measurement assembly 240 includes a printed circuit board (PCB) 241 including an orifice 242 extending through the PCB 241. An infrared (IR) sensor 243 is on the PCB 241. The IR sensor 243 transmits IR light 244 to a temperature measurement location 245 (e.g., a temperature measurement location 245 on the outer housing 247 of the motor 220) through the orifice 242 of the PCB 241. The orifice 242 provides an unobstructed optical path from the IR sensor 243 to the temperature measurement location 245. The orifice 242 may be filled with air or with a substantially transparent (to IR light) material such as transparent silicone. The IR sensor 243 detects IR light 244 reflected from the temperature measurement location 245 and back to the IR sensor 243 through the orifice 242 to determine a temperature of the temperature measurement location 245 (e.g., the temperature measurement location 245 on the outer housing 247 of the motor 220).

In an aspect of the present disclosure, the IR sensor 243 includes an IR filter 246. The IR sensor 243 transmits the IR light 244 through the IR filter 246. The IR filter 246 is on the PCB 241 and extends across the orifice 242 of the PCB 241. The IR filter 246 may be disposed directly on the PCB 241. The IR filter 246 is configured to selectively pass or block IR light and/or visible light based on the configuration of the IR sensor 243. Thus, the IR filter 246 may increase the sensitivity and accuracy of the IR sensor 243.

In an aspect of the present disclosure, the IR sensor 243 is positioned to transmit IR light 244 across air gap 248 between the PCB 241 and the temperature measurement location 245.

In an aspect of the present disclosure, a substantially transparent spacer 249 is positioned between the PCB 241 and the temperature measurement location 245. The substantially transparent spacer 249 may be formed of or may include silicone, such as transparent silicone.

As an example, the substantially transparent spacer 249 may be disposed on the motor 220, such as on the outer housing 247 of the motor 220. The IR sensor 243 transmits the IR light 244 across the substantially transparent spacer 249 to the temperature measurement location 245 (e.g., to the temperature measurement location 245 of the motor 220).

The IR sensor 243 may detect a surface temperature 245 at a gap distance 250 of up to 1 meter, and thus the air gap 248 or the transparent spacer 249 may each span a distance of up to 1 meter between the IR sensor 243 and the temperature measurement location 245.

In an aspect of the present disclosure, an output coupler 218 is operably coupled to the motor 220, and the IR sensor 243 transmits IR light 244 to a temperature measurement location 245 of the output coupler 218 to determine a surface temperature of the temperature measurement location 245 of the output coupler 218.

Referring particularly to FIG. 3, component 251 may be disposed in handpiece 212. Component 251 may be a component of the handpiece other than the motor 220 or the output coupler 218. Thus, the temperature measurement assembly 240 may be employed to measure a surface temperature of any component in handpiece 212 that is accessible through an air gap (e.g., air gap 248) or through an optically transparent pathway (e.g., through transparent spacer 249) between the temperature measurement assembly 240 and the component 251 across a gap distance 250.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended thereto.

What is claimed is:

1. A surgical instrument, comprising:
   a handpiece including a housing, a motor disposed in the housing, and an output coupler engaged to and axially fixed relative to the motor within the housing and extending from the motor, the output coupler configured to connect to an end effector assembly when the end effector assembly is operably coupled to the handpiece to enable the motor to actuate the end effector assembly; and
   a temperature measurement assembly disposed in the housing, the temperature measurement assembly configured to measure a temperature of the output coupler at a temperature measurement location on the output coupler, the temperature measurement assembly including:
   a printed circuit board (PCB) including at least one orifice extending through the PCB; and
   an infrared (IR) sensor disposed on the PCB, the IR sensor configured to transmit IR light to the temperature measurement location on the output coupler through the at least one orifice of the PCB, and the IR sensor configured to detect IR light reflected from the temperature measurement location on the output coupler to determine a temperature of the temperature measurement location on the output coupler.

2. The surgical instrument of claim 1, wherein the IR sensor further includes an IR filter, and wherein the IR sensor transmits the IR light through the IR filter.

3. The surgical instrument of claim 2, wherein the IR filter is disposed on the PCB and extends across the at least one orifice of the PCB.

4. The surgical instrument of claim 1, wherein the IR sensor is positioned to transmit IR light across an air gap between the PCB and the temperature measurement location on the output coupler.

5. The surgical instrument of claim 1, further including a substantially transparent spacer between the PCB and the output coupler, wherein the IR sensor transmits the IR light across the substantially transparent spacer to the temperature measurement location on the output coupler.

6. The surgical instrument of claim 5, wherein the substantially transparent spacer is formed of silicone.

7. A surgical instrument, comprising:
   a handpiece including a housing, a motor disposed in the housing, and an output coupler engaged to and axially fixed relative to the motor within the housing and extending from the motor; and
   an end effector assembly including an input coupler configured to releasably engage the output coupler, wherein the motor is configured to drive the output coupler to thereby drive the input coupler to actuate the end effector assembly,
   wherein the handpiece further includes a temperature measurement assembly disposed in the housing, the temperature measurement assembly configured to measure a temperature of the output coupler at a temperature measurement location on the output coupler within the housing of the handpiece, the temperature measurement assembly including:

a printed circuit board (PCB) including at least one orifice extending through the PCB; and an infrared (IR) sensor disposed on the PCB, the IR sensor configured to transmit IR light to the temperature measurement location on the output coupler through the at least one orifice of the PCB, and the IR sensor configured to detect IR light reflected from the temperature measurement location on the output coupler to determine a temperature of the temperature measurement location on the output coupler.

8. The surgical instrument of claim 7, wherein the IR sensor further includes an IR filter, and wherein the IR sensor transmits the IR light through the IR filter.

9. The surgical instrument of claim 8, wherein the IR filter is disposed on the PCB and extends across the at least one orifice of the PCB.

10. The surgical instrument of claim 7, wherein the temperature measurement location on the output coupler is on an outer surface of the output coupler.

11. The surgical instrument of claim 7, wherein the IR sensor is positioned to transmit IR light across an air gap between the PCB and the temperature measurement location on the output coupler.

12. The surgical instrument of claim 7, further including a substantially transparent spacer between the PCB and the output coupler, wherein the IR sensor transmits the IR light across the substantially transparent spacer to the temperature measurement location on the output coupler.

13. The surgical instrument of claim 12, wherein the substantially transparent spacer is formed of silicone.

\* \* \* \* \*